(12) United States Patent
Crapser (10) Patent No.: US 9,352,093 B2
(45) Date of Patent: May 31, 2016

(54) VACUUM RETRACTABLE SYRINGE SAFETY DEVICE

(75) Inventor: Andrew Chase Crapser, Quechee, VT (US)

(73) Assignee: The Lexington Group, L.L.C., Paxton, MA (US)

( * ) Notice: Subject to any disclaimer, the term of this patent is extended or adjusted under 35 U.S.C. 154(b) by 2483 days.

(21) Appl. No.: 12/102,177

(22) Filed: Apr. 14, 2008

(65) Prior Publication Data

US 2008/0255514 A1 Oct. 16, 2008

Related U.S. Application Data

(60) Provisional application No. 60/911,615, filed on Apr. 13, 2007.

(51) Int. Cl.
| | |
|---|---|
| *A61M 5/50* | (2006.01) |
| *A61M 5/28* | (2006.01) |
| *A61M 5/32* | (2006.01) |
| *A61M 5/34* | (2006.01) |
| A61M 5/31 | (2006.01) |
| A61M 5/315 | (2006.01) |

(52) U.S. Cl.
CPC .......... *A61M 5/28* (2013.01); *A61M 5/322* (2013.01); *A61M 5/344* (2013.01); *A61M 5/348* (2013.01); *A61M 5/502* (2013.01); *A61M 2005/3104* (2013.01); *A61M 2005/3128* (2013.01); *A61M 2005/31508* (2013.01); *A61M 2005/3206* (2013.01); *A61M 2005/3239* (2013.01)

(58) Field of Classification Search
CPC ..... A61M 5/322; A61M 5/502; A61M 5/344; A61M 5/348; A61M 5/3294; A61M 5/31596; A61M 5/3134; A61M 5/31515; A61M 2005/3128; A61M 2005/3206; A61M 2005/3239; A61M 2005/31508; A61M 2005/3142; A61M 2039/2486; A61M 5/31578; F16K 1/10; F16K 1/2265; F16K 1/305; F61K 3/0281; F61K 3/316; F61K 3/182; F61K 3/18; F61K 3/10
See application file for complete search history.

(56) References Cited

U.S. PATENT DOCUMENTS

| | | | | |
|---|---|---|---|---|
| 3,306,291 | A * | 2/1967 | Burke | 604/110 |
| 5,057,087 | A * | 10/1991 | Harmon | 604/198 |
| 5,122,124 | A | 6/1992 | Novacek et al. | |
| 5,188,601 | A | 2/1993 | King | |
| 5,195,526 | A * | 3/1993 | Michelson | 600/431 |
| 5,298,024 | A * | 3/1994 | Richmond | 604/90 |
| 5,304,150 | A | 4/1994 | Duplan et al. | |
| 5,336,183 | A * | 8/1994 | Greelis et al. | 604/97.03 |
| 5,346,474 | A | 9/1994 | King | |

(Continued)

*Primary Examiner* — Nathan R Price
*Assistant Examiner* — Justin L Zamory
(74) *Attorney, Agent, or Firm* — Maine Cernota & Rardin (57) ABSTRACT

A safety syringe with a plunger in which a needle is attached to a mobile component that is mechanically not linked to the plunger but is slidable within the barrel of the syringe and has a valve mechanism for opening a port connecting the interior volume between the mobile component and the plunger to the needle bore. The mobile component is first pushed by the plunger to the bottom of the barrel so that the needle extends normally, the mobile component is mechanically locked in place for use conventionally, and the needle bore is opened. After use, the needle bore may be closed, the lock released, and the mobile component and attached needle sucked back into the barrel by pulling the plunger out, retracting the used needle into the barrel. There may be a plunger lock. There may be an upper barrel locking position for the mobile component.

19 Claims, 11 Drawing Sheets

(56) References Cited

U.S. PATENT DOCUMENTS

| | | |
|---|---|---|
| 5,445,620 A | 8/1995 | Haber et al. |
| 6,059,756 A | 5/2000 | Yeh |
| 6,077,245 A | 6/2000 | Heinrich et al. |
| 6,171,285 B1 | 1/2001 | Johnson |
| 6,530,906 B2 | 3/2003 | Hu |
| 6,808,511 B2 | 10/2004 | Pond |
| 6,878,131 B2 | 4/2005 | Novacek et al. |
| 6,979,314 B2 | 12/2005 | Hsieh et al. |
| 7,090,657 B2 | 8/2006 | Tang |
| 7,682,345 B2 * | 3/2010 | Savage ............... A61M 5/007 604/151 |
| 2004/0230163 A1 * | 11/2004 | Chen ........................ 604/240 |

* cited by examiner

VACUUM RETRACTABLE SYRINGE SAFETY DEVICE

RELATED APPLICATIONS

This application claims the benefit of U.S. Provisional Application No. 60/911,615, filed Apr. 13, 2007, which is herein incorporated in its entirety by reference.

FIELD OF THE INVENTION

The present invention relates to a syringe, and more particularly to a safety syringe, which prevents injury and contamination during and after its service and is inexpensive to manufacture.

BACKGROUND OF THE INVENTION

In the health care clinical setting a "used" needle (a needle that has already punctured the skin of a patient) is a hazard to all clinicians and technicians who are exposed. Once contaminated by the patient, the sharp needle can then transmit infections to clinicians and technicians who are handling it, should they mistakenly puncture their own skin. This unintended puncturing of an exposed health care worker by a used needle is called a "needle-stick" injury, and is a leading occupational hazard in the health care setting. Between 600,000 to 800,000 needle-stick injuries occur within the hospital setting annually in the U.S., infecting healthcare workers with blood borne pathogens including HIV, HepB, and HepC. As of 2001, OSHA began requiring that all employers replace traditional syringes with safety devices. With the intensifying nationwide concern over reducing healthcare costs, the need has never been greater for a safety syringe that comprises ideal functionality while costing less to manufacture than products currently available.

SUMMARY OF THE INVENTION

The invention, simply stated, is a syringe with a mobile component to which a needle is or can be attached, positionable in a retracted position where the needle, if attached, is enclosed; and which is not mechanically linked to the plunger but can be moved by the plunger and locked in position for use as a conventional syringe. There are other aspects and advantages. In one aspect the invention provides a syringe that may be delivered to the user or administrator in a needle-retracted configuration for safe handling, where a mobile component within the barrel to which a needle is attached or attachable, may be deployed by use of the plunger for moving the mobile component longitudinally to the distal end of the barrel and locking it there for use as in the conventional manner.

In another aspect, the invention provides for retracting the mobile component with its attached needle back into the barrel or cylinder of the syringe by retracting the plunger.

In yet another aspect, the syringe may be filled and employed without ejecting the full dose of solution.

It is a further goal of the present invention to provide for a releasable locking mechanism that permits the mobile component to be moved multiple times between retracted (safe) and extended positions to allow for multiple injections for the same patient.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
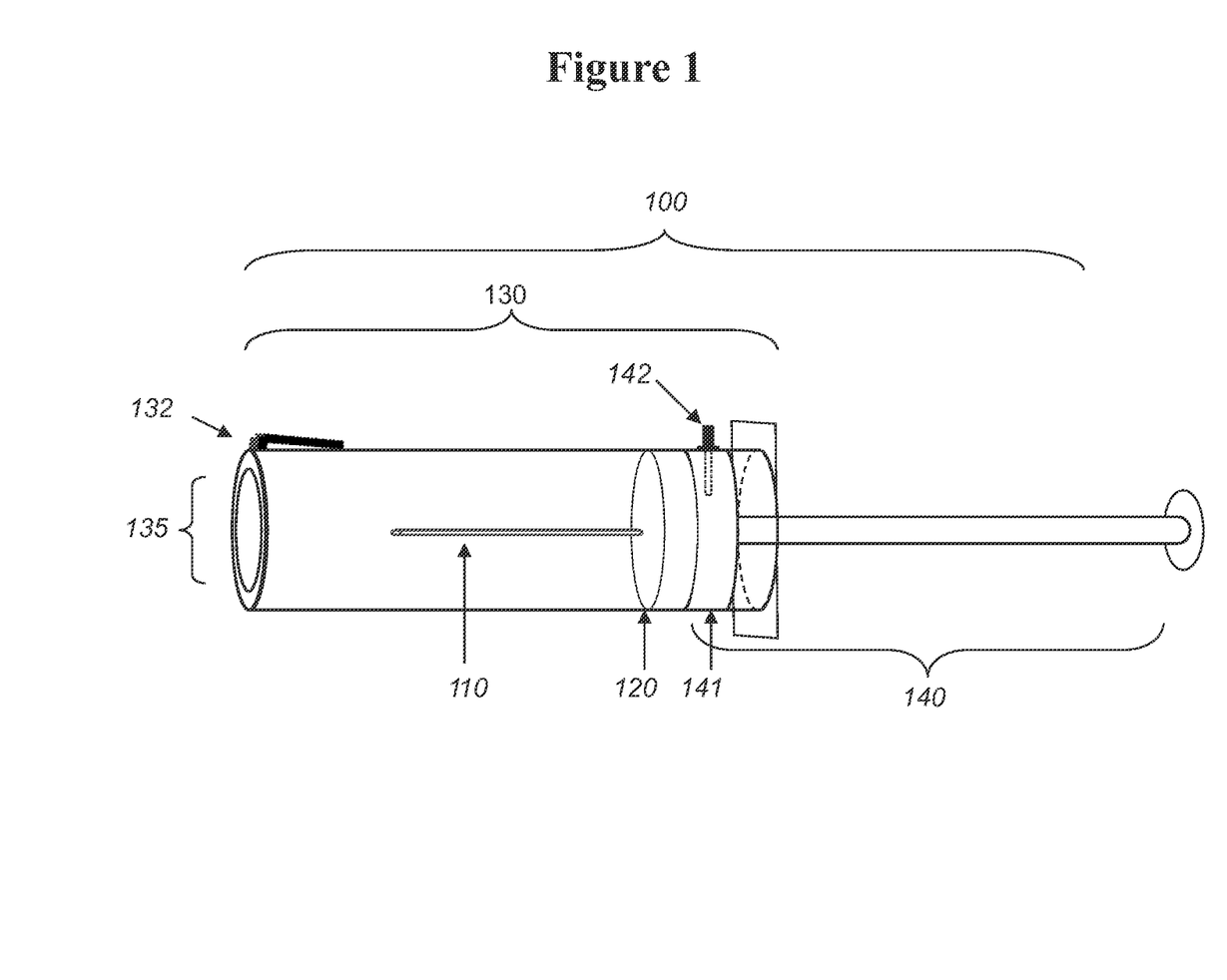
FIG. 1 is a perspective assembly view of a retractable syringe safety device with the needle and/or mobile component and the plunger in a retracted position; interior components shown here and in other figures in solid lines for clarity.

The invention is susceptible of many embodiments. For example, as shown in FIG. 1, in one embodiment a vacuum retractable syringe safety device of the present invention differs from the syringes of the prior art by having a needle 110 attached to a mobile component 120 which is configured to be sealingly and slidably moved within the interior length of barrel 130 of syringe 100, and a mechanically separate plunger 140, which is likewise configured to be sealingly and slidably moved within the interior length of barrel 100 by manipulation of its externally extending handle. Syringe 100 may or may not be configured with a plunger locking mechanism 142 by which plunger 140 is held in the up or cocked or retracted position until the plunger locking mechanism is released. The locking mechanism 142 may be a one-time device such as an external removable pin or key or fused link device, or a reusable or switchable device, the disabling of which permits plunger 140 to be depressed into the barrel. Barrel 130 is preferably cylindrical in shape, and has a constant interior wall cross section profile over its length. The barrel may be or have other geometrical shapes, externally and/or internally, as well. Barrel 130 has an opening 135 sized to pass needle 110 and expose the underside or lower side of mobile component 120 to atmospheric pressure.

Syringe 100, in the configuration of FIG. 1, with mobile component 120 and needle 110 encased within barrel 130, and plunger 140 in the retracted position, and optionally locked in the retracted position, is considered "safe" for handling. The syringe may be configured in this manner for shipping and storage, and initial handling prior to first use, and reconfigured in this manner during use if appropriate, and after use for final handling and disposal. Opening 135 may optionally be closed by a disposable or reusable seal or cap that must be removed prior to using the syringe.

Figure 2:
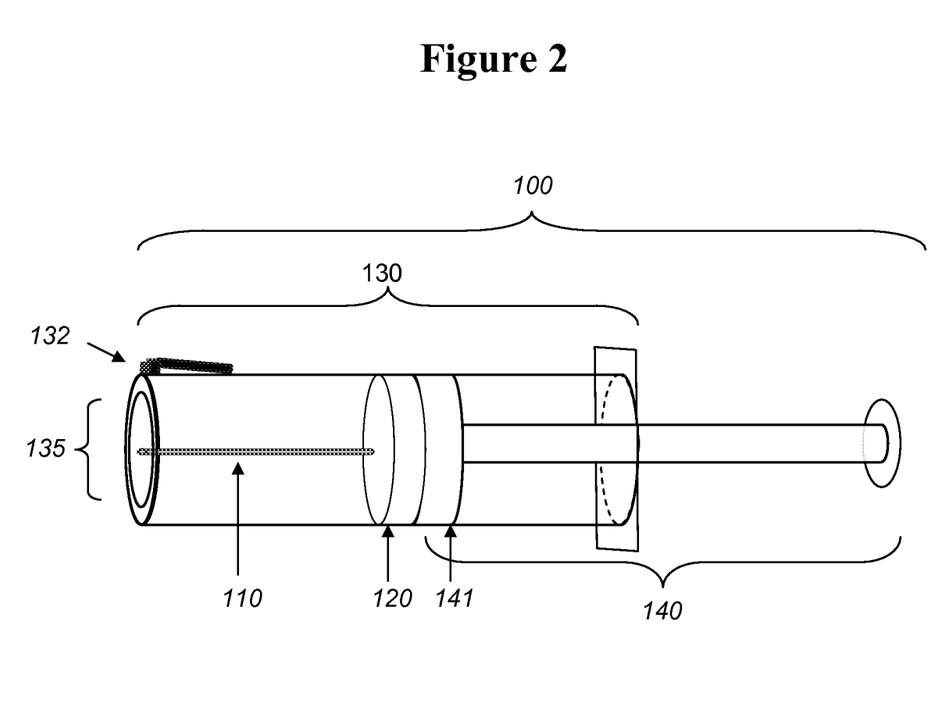
FIG. 2 is a perspective assembly view of the device of FIG. 1 with the needle or mobile component and the plunger in a mid-way position between needle and plunger retracted positions of FIG. 1 and needle or mobile component extended and plunger fully depressed positions.
Figure 3:
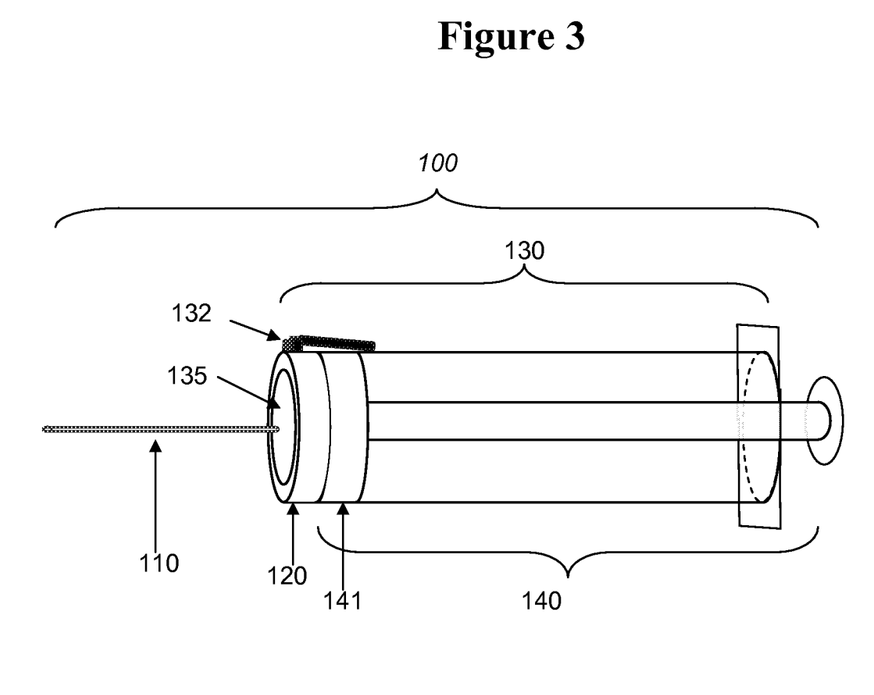
FIG. 3 is a perspective assembly view of the device of FIGS. 1 and 2 with the plunger and needle or mobile component pushed maximally forward to the distal end of the barrel, to the needle or mobile component extended position and plunger fully depressed position.
Figure 4:
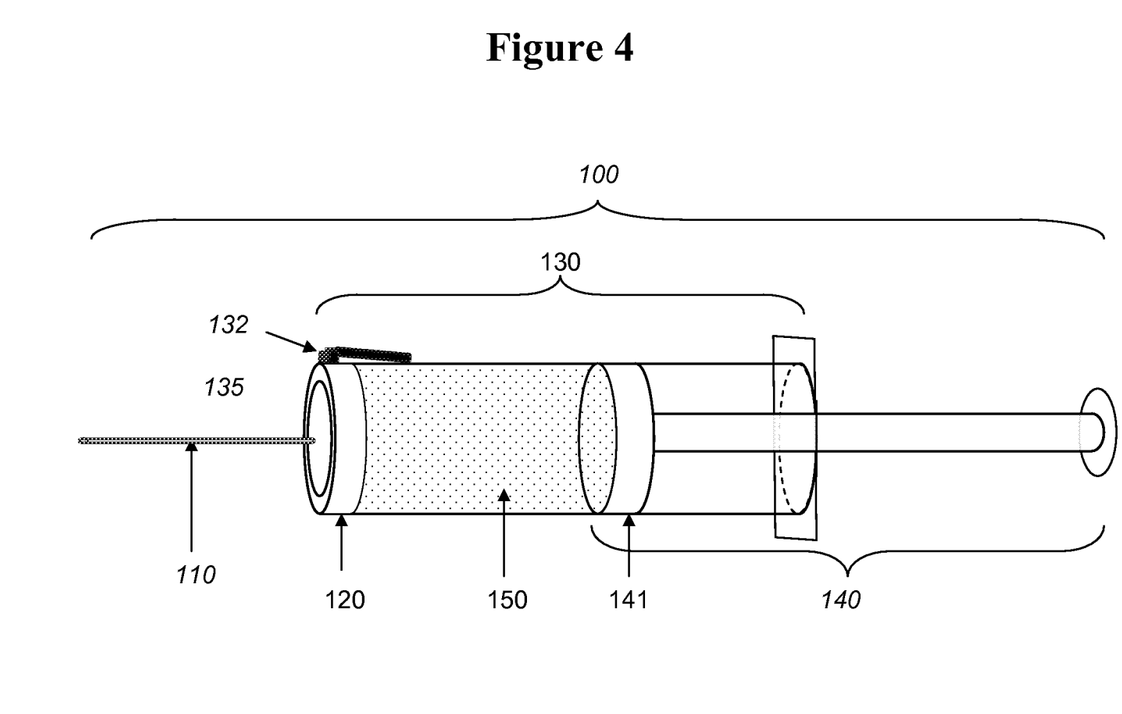
FIG. 4 is a perspective assembly view of the device of FIGS. 1-3, with the mobile component locked in the extended position and the plunger having been retracted midway so as to draw fluid into the barrel in the conventional fashion.

Referring to FIG. 2, depressing plunger 140 necessarily pushes adjacent mobile component 120 downward as well, towards the distal end of barrel 130. Referring to FIG. 3, mobile component 120 and attached needle 110 arrive at and snap lock into its final extended position at the distal end of barrel 130, by means of a locking mechanism that is further described below. Mobile component 120 remains locked in place at the end of syringe barrel 130 throughout the use of syringe 100. This allows syringe 100 to be operated as a standard, non-safety syringe. Referring to FIG. 4, the retracting of plunger 140 draws fluid 150 through needle 110 into barrel 130 in the conventional manner, and permits it to likewise be expelled in the conventional manner.

FIGS. 1-4 can also be viewed as a sequence of operation, in the context of the description above.

As illustrated in FIG. 4, the process of filling or loading the syringe with solution 150 is no different from the process of filling a normal, non-safety syringe: the safety syringe operates as a traditional non-safety syringe once the mobile component 120 is locked into place at the distal end of barrel 130.

The process of administering solution 150 to the patient is also no different from the process of administering solution from a normal, non-safety syringe. Similar to a normal, non-safety syringe, the clinician would puncture the skin of the patient with needle 110, push needle 110 to the desired depth, and then push plunger 140 forward using an appropriate amount of force to inject the desired amount of solution into the patient.

When the desired amount of solution 150 has been administered, the needle retraction process and function is initiated. Not all of the solution in the barrel is required to be ejected from the syringe in order for the needle retraction function to be employed. Any amount of solution up to the maximum capacity of the device can remain in the barrel.

Figure 5:
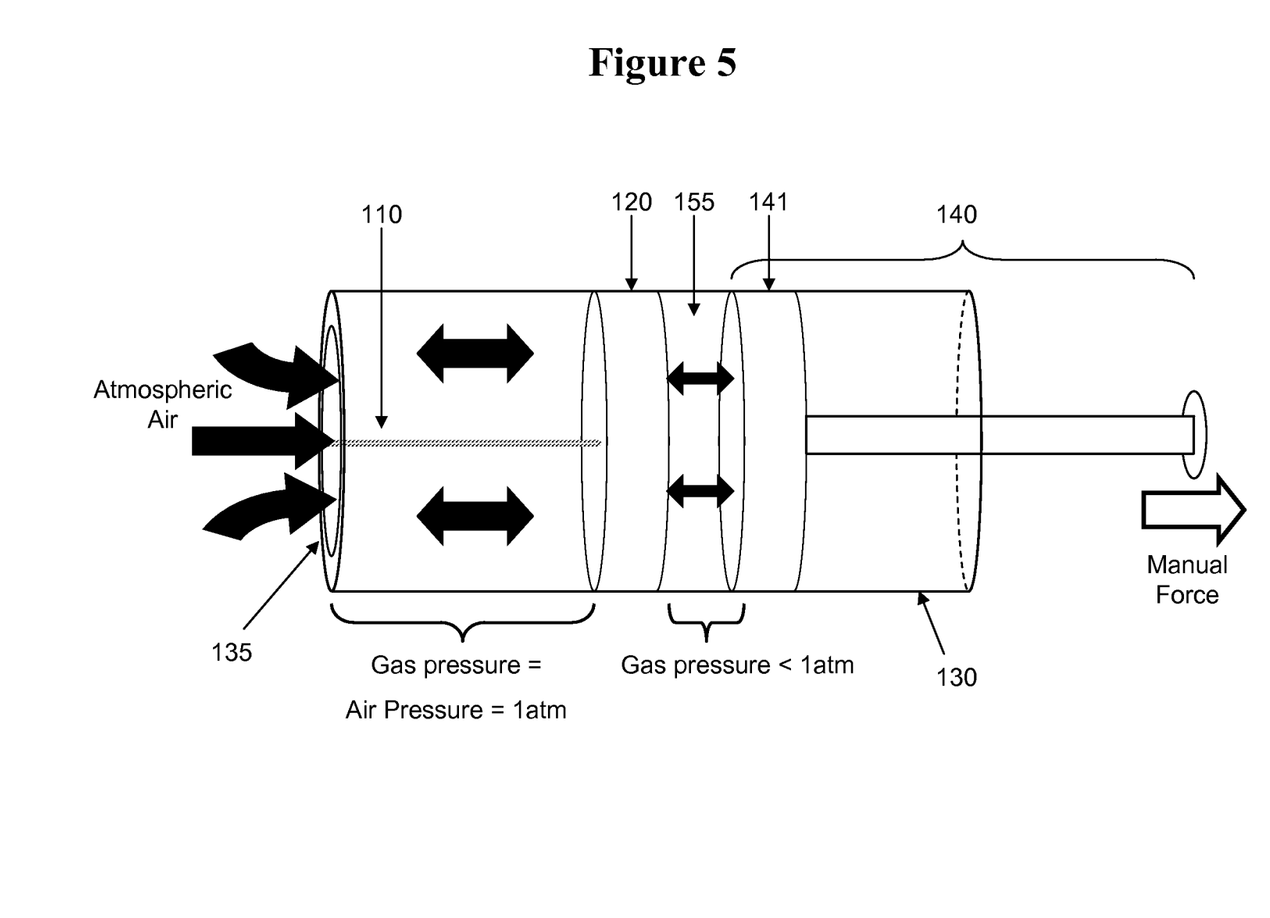
FIG. 5 is a perspective assembly view adjusted and diagramed to illustrate the atmospheric pressure forces enabling retraction of the mobile component by use of the plunger in the absence of a mechanical bond or linkage.
Figure 6:
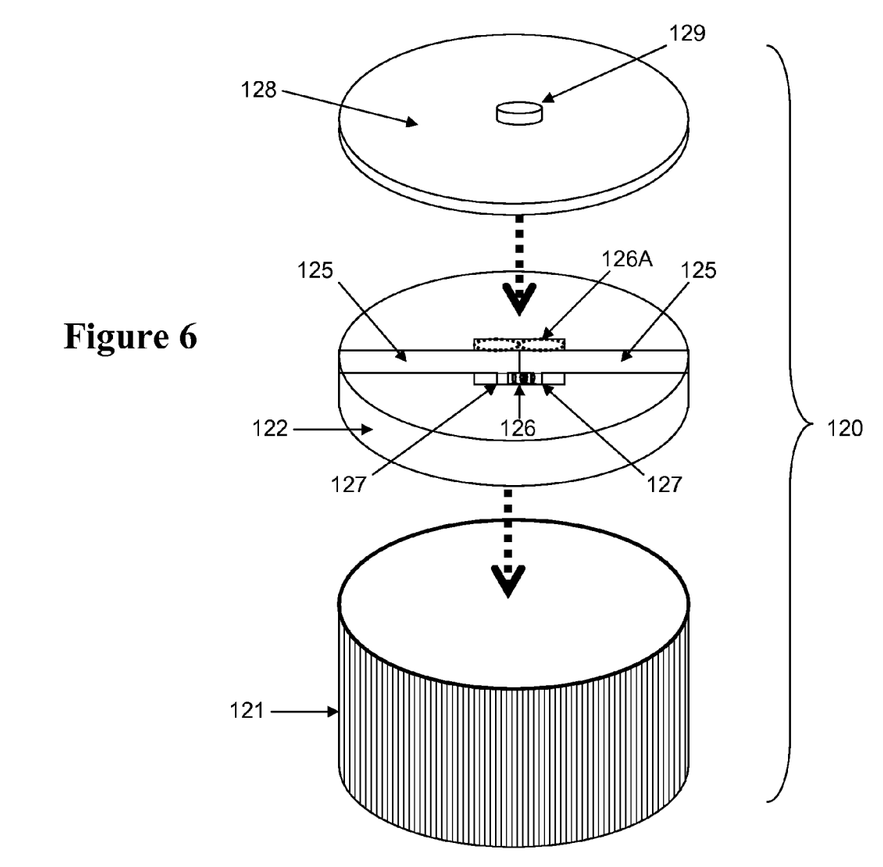
FIG. 6 is a perspective exploded view of selected sub-components that comprise a mobile component of one embodiment of the device.
Figure 7A:
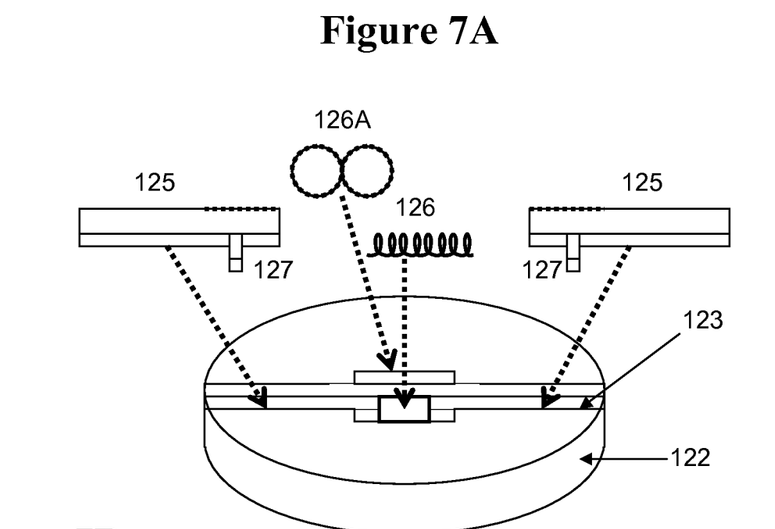
FIG. 7A is an exploded perspective view of selected components of the mobile component of one embodiment of the device.
Figure 7B:
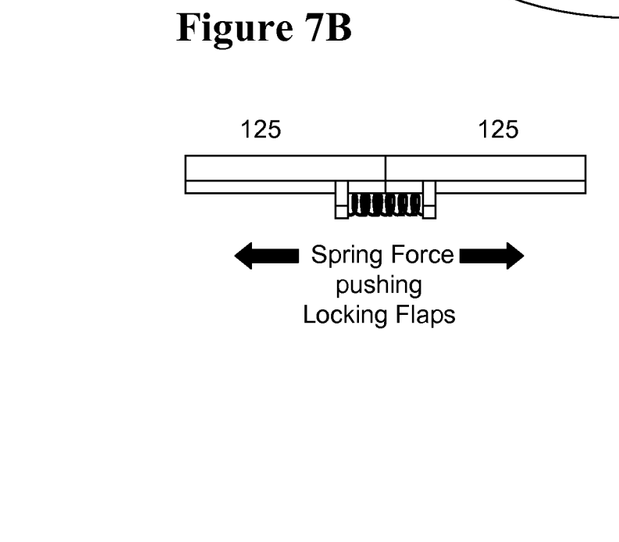
FIGS. 7B and 7C are side elevation views of the sliding lock and orifice valve mechanism of FIG. 7A in respective unlocked-closed and locked-open positions.
Figure 7C:
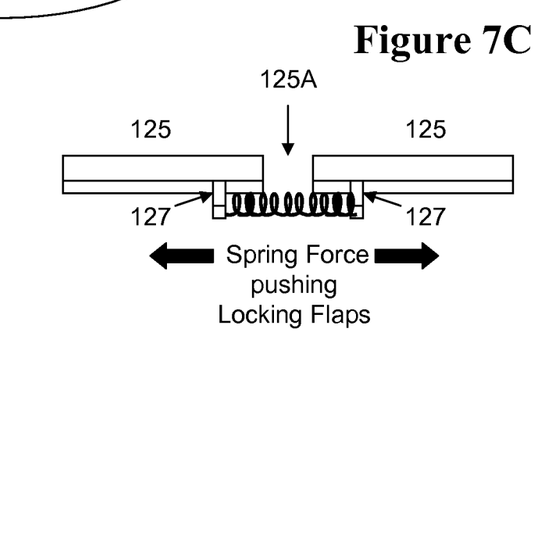
Figure 8:
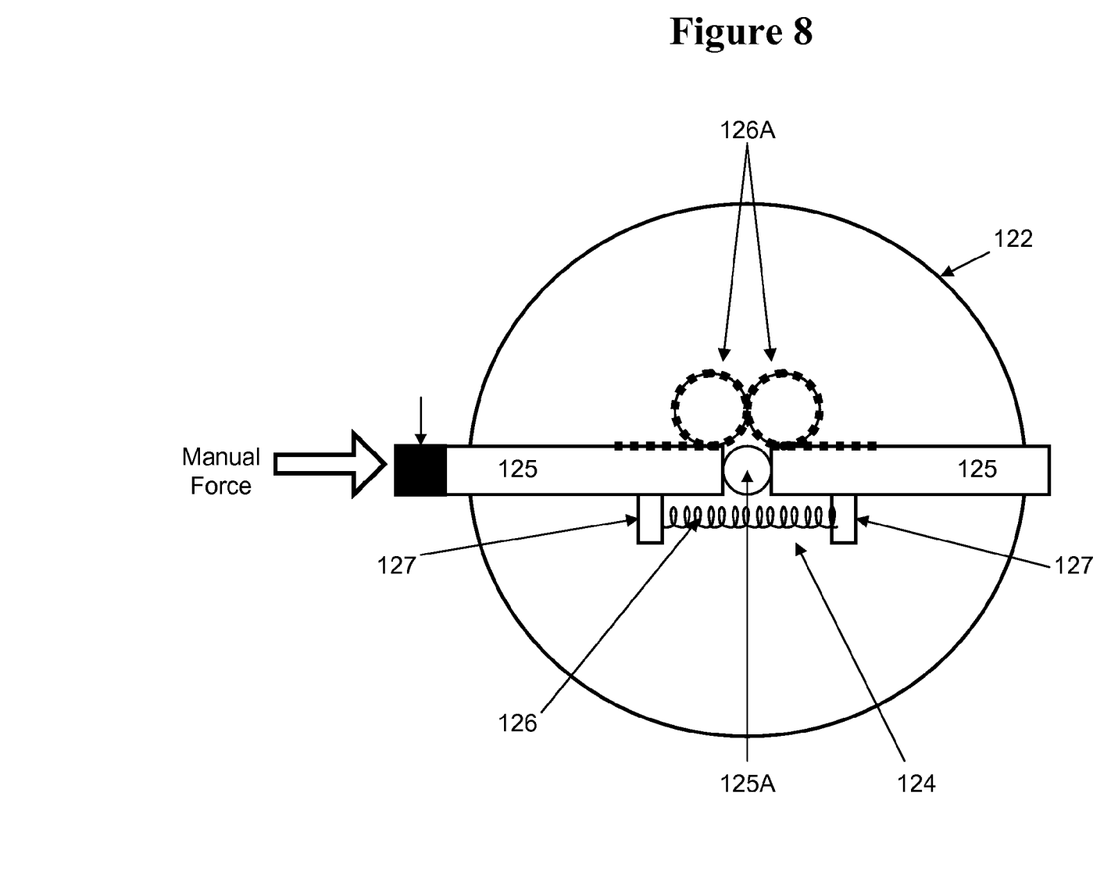
FIG. 8 is a top view of the selected components of FIG. 7A, illustrated in their assembled position with the interlocked slide lock bars in the extended position so that the orifice is open.

Referring now to FIGS. 3, 4, and 5, the needle retraction process and function is illustrated and explained. Any, as in FIG. 4, or no, as in FIG. 3, residual volume of solution 150 may remain in the syringe between mobile component 120 and plunger 140, without interfering with the needle retraction process. First, release lever 132 is depressed so as to retract the mobile component locking mechanism and close the orifice leading to the needle bore, which as is further illustrated in other figures and described below. This closes the needle bore and prevents any change in the volume of air or fluid between mobile component 120 and plunger 140. Referring to FIG. 5, when plunger 140 is then manually retracted in the conventional manner, mobile component 120 and attached needle 110 are drawn by the resulting reduced fluid pressure between mobile component 120 and plunger 140, upwards into barrel 130, thereby retracting the mobile component 120 and needle 110. Plunger 140 may optionally be locked in the retracted position so as to make "safe" the syringe until needed for reuse or disposal.

It will be readily apparent that there is some advantage to embodiments having barrel 130 of sufficient length to contain a full dose of solution, meaning the length of a "draw stroke" of the plunger for extracting a full dose from the solution source, plus the length of the needle. This provides for the syringe to be filled in the conventional manner and the mobile component then released from its locked position and retracted to where the needle tip is fully within the barrel for safe handling prior to re-extending the mobile component and administering the first dose of solution. Other embodiments may have shorter barrels relative to their fluid capacity, length of needle and draw stroke, and still enjoy many benefits of the invention.

Following contamination of the needle by the puncturing of the patient's skin, mobile component 120 and attached needle 110 may be manually released from the locked position and then retracted. FIGS. 2 and 5 illustrate the position of needle 110 and mobile component 120 during mid-retraction. FIG. 1 illustrates the position of needle 110 and mobile component 120 after retraction is complete. Conventional extraction of needle 110 from the patient can be achieved by pulling syringe 100 away from the patient, as done with a normal, non-safety syringe. The safety retraction mechanism of the device can be employed following complete extraction of needle 110 from the patient.

However, the device also allows for use of the needle retraction safety mechanism while needle 110 is still in the patient, extracting the needle from the patient directly into the barrel of the syringe, thus preventing needle 110 from being exposed to the external environment while needle 110 is being extracted from the patient's skin. In the former situation, mobile component 120 remains in the locked position while needle 110 is being removed from the patient, exposing the needle for possible unintended re-puncture of the patient or jury to the administrator, or other contact that might further contaminate the needle. In the latter situation, mobile component 120 is unlocked while needle 110 is still inside patient, and the retracting plunger easily withdraws the mobile component and needle with it. Either way, once mobile component 120 is unlocked, both mobile component 120 and needle 110 are drawn back into barrel 130 of the syringe by pulling plunger 140 in the backward direction.

As shown in FIG. 5, the mechanism of extension and retraction of the mobile component using the mechanically separate plunger exploits simple rules of pressure and volume. The volume between plunger stopper 141 and mobile component 120 is fixed when the lock mechanism is released, so that the extension or retraction pressure on plunger 140 is transmitted by the fixed volume 155 to mobile component 120, extending or drawing that component back into the barrel concurrently with plunger motion. This assumes, of course, that the seals and bore valve are functional so that there is no significant leakage by the seals or through the bore valve when tension or pressure is applied to the plunger.

As seen in FIG. 1-5, barrel 130 consists of a partially open end 135 which exposes the distal side of mobile component 120 to atmosphere air outside barrel 130. When mobile component 120 is locked at the distal end of barrel 130, there is an opening, or "solution canal" 125A, that allows solution to pass between barrel 130 and needle 110 through the needle bore during the ejection or drawing of solution. When mobile component 120 is unlocked and therefore free to move linearly within barrel 130 (as illustrated in FIGS. 1, 2 and 5), this solution canal 125A is blocked, preventing air or fluid from entering space 155 and holding the contained volume constant during retraction and re-extension. Solution canal 125A is only open when mobile component 120 is locked in place at the distal end of barrel 130.

In the illustrated embodiments, the blocking and unblocking of solution canal 125A is synchronized with the locking system of mobile component 120, as described below. It will be appreciated that other embodiments may uncouple these functions, or provide alternative logic to their respective operations so that, for example, the needle bore may be opened and/or closed by a separate release mechanism, but only when the mobile component lock is engaged. Extending on that example, by way of a further example, when the mobile component is locked in the extended position, the opening to the solution canal and needle bore for release of solution may be triggered by increasing plunger pressure and thereafter close again when plunger pressure is released, or when full plunger stroke is achieved. Simple pressure release valves are known to provide this type of functionality.

Significant forces at work during the retraction process include: atmospheric pressure pushing mobile component 120 in the axial direction back into barrel 130; the static and kinetic friction of the seals of mobile component 120 and plunger stopper 141 with respect to the interior wall surface of barrel 130; and the force being applied to the plunger 140 and transmitted to mobile component 120 by the fixed volume of fluid between them.

Once some or all solution in barrel 130 has been injected into the patient and employment of the safety mechanism is desired, the administrator will unlock or release mobile component 120 from its fixed position by pressing on lever 132 at the distal end of barrel 130, and begin pulling plunger 140 backward. In doing so, the pressure of the contained space 155 is reduced relative to atmospheric pressure, thus creating suction on mobile component 120, allowing atmospheric pressure to push mobile component 120 back into barrel 130.

It should be noted that the function of lever 132 may be duplicated by an external rotatable ring on barrel 130, that by manual rotation engages one or more of the protruding lock bars and depresses them radially or non-radially inward so as to unlock the mobile component to move within the barrel. Alternative, barrel 130 may be equipped with a slideable release ring that by longitudinally sliding on barrel 130 likewise engages one or more protruding lock bars and depresses them sufficiently to release their grip on the barrel. Other and various externally manipulated release mechanisms will be readily apparent to one of ordinary skill in the art, and are within the scope of the invention.

Figure 11:
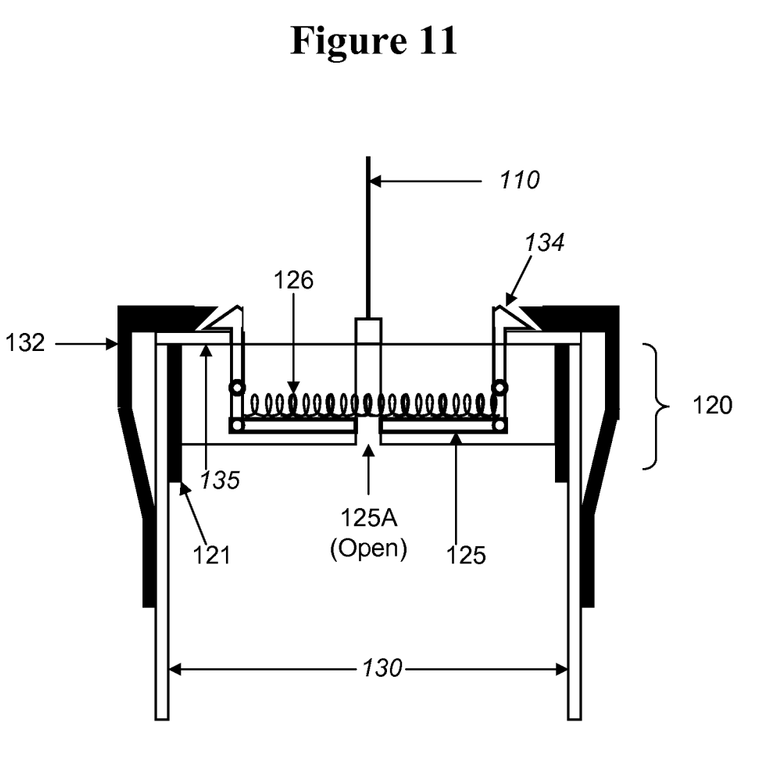
FIG. 11 is a cross section view of the distal end of one embodiment of a syringe of the invention, illustrating a longitudinally extending mobile component, spring loaded locking mechanism that latches to the barrel end flange and is released by squeezing an external ring that bears radially inward on the locking hooks.

For example, referring to FIG. 11, the distal end of barrel 130 is flanged inwardly so that the diameter of the opening of barrel end 135 is of a smaller diameter than that of mobile component 120, but larger than the diameter of needle 110, so as to prevent mobile component 120 from moving beyond its farthest point in the distal direction, but still freely allow air to be admitted into and out of the lower end of barrel 130 during operation of the mobile component retraction and extension functions. The locking mechanism in this embodiment is configured to extend longitudinally downward from the mobile component with one or more spring loaded, pawl-shaped hooks 134, preferably but not necessarily a pair of opposing hooks, pivotally mounted to mobile component base 122 and radially oriented to be inwardly compressed as they ride over the flange lip of barrel end 135, and then partially re-extend under pressure of spring 126, as they hook on the flange lip, thereby locking mobile component 120 in position within barrel 130. The opposite end of hooks 134 are pivotally connected to locking bars 125, which in this embodiment are limited to their port valve function, normally keeping port 125A closed but upon engagement of the mobile component with the barrel end by action and motion of hooks 134, slid apart to open port 125A to fluid flow.

Regarding the barrel end opening 135, in alternate embodiments the central diameter of barrel end 135 may more closely conform to the external needle diameter for support or otherwise, and there may be other ventilation holes and/or latching holes or recesses in the barrel end flange to accommodate air flow and/or longitudinally extending latching hooks as described above.

Also, as is well understood in the art, as in a conventional syringe an air seal at the top of the barrel around the plunger handle must be avoided. The proximate or upper end of the barrel must be ventilated in some manner above the plunger stopper upper travel limit, as around the plunger handle, to permit airflow into and out of the top of the barrel above the plunger stopper in concert with plunger motion.

Mobile component 120 may or may not require lubrication, which is likewise true of rubber stopper 141 on plunger 140, to minimize the frictional forces as it slides up and down barrel 130 of the syringe. Efficient retraction of mobile component 120 and needle 110 requires good barrel wall seals on the sliding components, with minimal friction or resistance to sliding between mobile component 120 and the inside of barrel 130 in particular. Stated otherwise, in the vacuum retractable syringe safety device, the coefficients of static and sliding/kinetic friction of the selected sealing materials of mobile component 120 and the inside surface of syringe barrel 130 must be relatively small. In the traditional syringe as well as in syringes of the invention, the rubber stopper on the plunger that makes contact with and seals the walls of the barrel, the equivalent of plunger stopper 141 of these embodiments, may or may not be lubricated.

It should be noted that syringe 100 may be packaged with needle 110 already attached to mobile component 120, and already retracted within barrel 130, with barrel end 135 optionally sealed, thus eliminating the need for an additional plastic needle cover that a separate and attachable needle would require. However, needle 110 may also be attached as a separate component after mobile component 120 is locked into place. The syringe may be adapted to accept a variety of needle sizes.

Traditional syringes are packaged either with needles pre-attached or separate from the needles. When needles are packaged separately, they are manually screwed onto the end of the barrel. Embodiments of the invention have the capability of having needle 110 screwed into needle base 129 of mobile component 120 after mobile component 120 is locked into place at the distal end of barrel 130. Therefore, whether or not the needle was pre-attached or added at the time of service to the mobile component, the operation of the device is the same.

In one embodiment of the invention, the connection between needle base 129 and needle 110 is identical to the universally standardized screw-on connection between needles and non-safety syringes. This allows each vacuum retractable syringe safety device to be compatible with all needle lengths/sizes (as separate parts). This compatibility is more useful, however, when the syringe is pre-packaged without a needle because it is not ideal to have to remove a first needle (especially one without a cover) from a syringe to replace it with different needle.

There are a number of alternative ways in which the locking function for the mobile component can be accomplished. One embodiment provides a locking mechanism that holds mobile component 120 in place at the distal end of the syringe barrel 130 in the manner illustrated in FIGS. 6-10. As illustrated, mobile component 120 comprises a collar 121 within which is contained a base plate 122 and a cover plate 128, the planes of which are perpendicular to the axis of collar 121. Radially oriented slots 123 in base plate 123 intersect at port 125A, which extends through base plate 122 and cover plate 128. Openings 121A in collar 121 are configured to be aligned with the outboard end of slots 123. Locking bars 125 are slidably contained in slots 123 by cover plate 128, and are sized to engage and functionally close off port 125A when retracted, with their outboard ends being flush with or slightly inboard of the exterior surface of collar 121.

A spring 126 is held in compression between tabs 127 on locking bars 125 so as to push them normally outward. In this embodiment, a gear set 126A is provided to interlock bars 125 so that they are constrained to extend or retract together, assuring a uniform locking function when extended and a uniform closure of port 125A when retracted. It will be appreciated that in other embodiments, fewer or more locking bars may be used, and also other locking bar interlock mechanisms, or no interlock mechanism, may be used.

At any location of the mobile component other than fully extended, locking bars 125 bear lightly on the inner wall of barrel 130 under pressure of spring 126. There are corresponding lock slots 132A on the distal end of barrel 130. When mobile component 120 is pushed to the end of barrel 130 where it reaches its flange stop, locking bars 125 come into alignment with lock slots 132A and are free to extend under pressure of spring 126, sufficiently far to lock mobile component 130 in position within the barrel. For embodiments equipped with a hard linked (two-way) locking bar interlock mechanism, the bars will necessarily extend together if all are clear and able, and retract together if any one is pushed back. For embodiments equipped with a return only interlock system, the bars will extend independently, each if it is clear and able, but the positive retraction of any one locking bar will retract the full set.

It will be readily apparent from FIGS. 1-5 to one of ordinary skill in the art that the retraction function can be exercised with a full or partial load of fluid in the barrel, either before or following an initial injection, if the barrel is of sufficient length.

Figure 9:
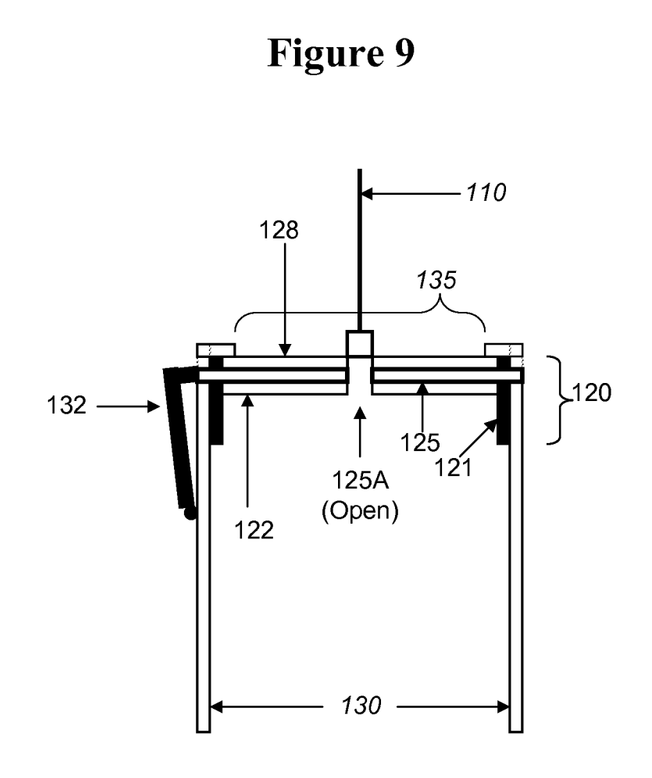
FIG. 9 is a diagrammatic cross section view of a mobile component armed with a needle and positioned at the distal end of a syringe barrel, illustrating the locking system in the locked position with orifice open as in FIG. 8, with the external release lever configured for depressing a sliding lock bar.
Figure 10:
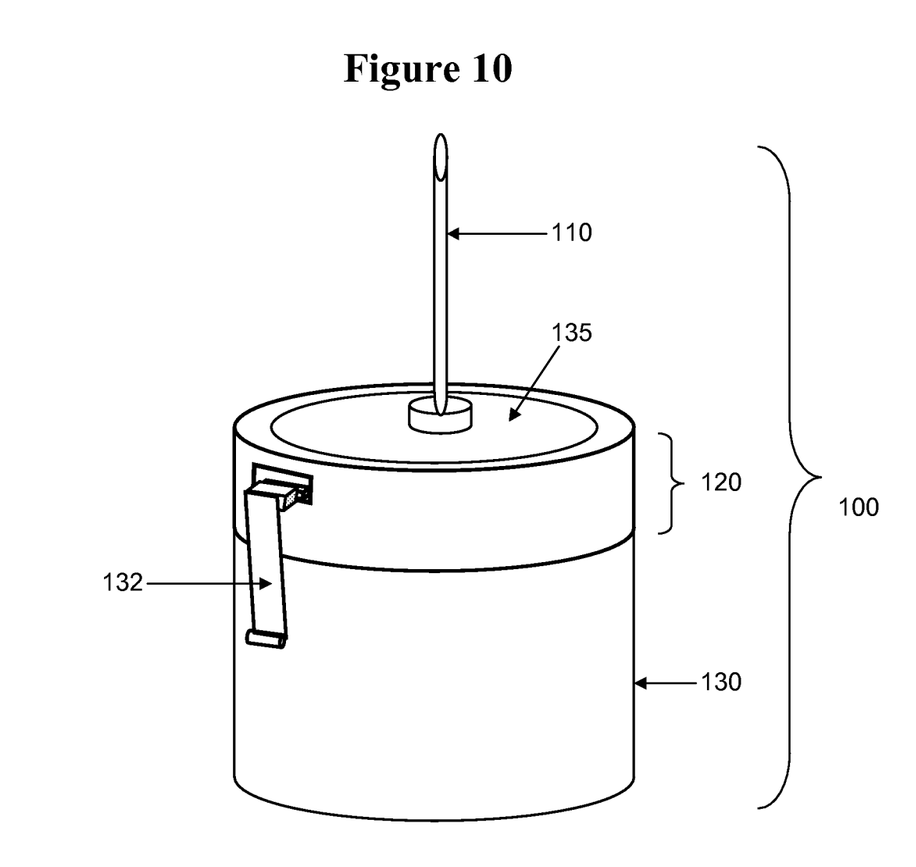
FIG. 10 is a perspective external view of the distal end of one embodiment of a syringe of the invention, illustrating the external release lever located at the outboard end of a locking bar of the mobile component.

FIGS. 9 and 10 disclose one embodiment of the invention having an externally accessible lever 132 by which the administrator may disengage the locking mechanism from the mobile component to allow for retraction of the mobile component and needle. Depressing the lever pushes locking bar 125 inward so that it is clear of locking slot 132A. An interlocking gear set causes any other locking bars to be retracted at the same time. The retraction of the locking bars has two important consequences; port 125A is closed whereby the interior volume between the plunger stopper 141 and the mobile component is held constant, and the mobile component is unlocked and free for being retracted by retracting motion of the plunger.

In other embodiments, there may be an upper mobile component locking position in the proximal end of the barrel that is structurally and functionally similar to the distal end locking mechanism, with upper locking slots in the barrel wall and upper release levers. This may be used as an initial or starting position, or a final, post-injection position, where the needle is fully enclosed.

Other and numerous simple lock and release systems are clearly possible to one of ordinary skill in the art, without necessity of being illustrated in detail. For example, there may be configured on the underside or outboard face of the mobile component one or more longitudinally extending spring loaded locking pawls or hooks, off set from the center of the mobile component or otherwise clear of the needle, that engage a locking slot or flange at the barrel end, optionally causing the fluid port to be opened to the needle bore. Such locking mechanisms may be similarly released by application of an externally applied release force at the distal end of the barrel so as to close the port and allow retraction of the mobile component.

As previously described, other and numerous mechanisms may be employed in other embodiments for affecting the unlocking of the locking bars constraining the mobile component. One of ordinary skill in the art will appreciate that such mechanisms may extend up the barrel to where they are more easily accessed and actuated by a digit of the same hand holding the syringe.

And yet, upon exposure to this disclosure, one of ordinary skill in the art will readily appreciate that there are other and numerous embodiments within the scope or equivalent to the claims appended here to. For example, there is a safety syringe that has a barrel; a plunger; and a mobile component; where the barrel has a proximate end and a distal end, the distal end is configured with a mobile component stop such as an inwardly flanged end or other structural interference with longitudinal travel of the mobile component, and a needle opening. The plunger is configured with a plunger stopper slidingly and sealingly engaged within the barrel, with a plunger handle extending from the proximate end of the barrel by which the plunger stopper may be moved longitudinally within the barrel as in a conventional syringe. The mobile component is slidingly and sealingly engaged within the barrel and configured with a fluid port connecting an inboard face facing the plunger stopper with an outboard face facing the distal end of the barrel. The outboard face is configured to accept attachment of a syringe needle whereby the axial bore through the needle is in communication with the port.

The mobile component and the barrel are cooperatively configured with a lock and release mechanism such as has been described elsewhere herein, whereby the mobile component is lockable in a fixed position at the distal end of and within the barrel, and is releasable thereafter for longitudinal motion within the barrel. The fluid port may have a valve mechanism operable to open and close the port to fluid flow.

In yet another embodiment, the lock and release mechanism and the valve mechanism may be cooperatively linked such that opening of the port to fluid flow occurs with locking of the mobile component in the fixed position and closing of the port to fluid flow occurs with release of the mobile component for longitudinal motion As another example, one embodiment may have a lock and release system where the mobile component is configured with at least one locking bar that is extendable radially outward beyond the inner diameter of the barrel, or downward into the barrel end structure, by operation of the plunger directly or indirectly, for engagement with the barrel for locking, and is releasable by operation of an externally accessible release mechanism on the barrel for releasing the locking pawl or bar. Depressing the plunger directly or indirectly pushes the mobile component to the far end of the barrel. The plunger stopper either contacts the mobile component directly if the syringe is empty or compresses whatever fluid is in the syringe thereby pushing the mobile component to the end of the barrel. The arrival of the mobile component at the distal end of the barrel triggers a lock mechanism, bar, hook or pawl, by any of numerous means such as but not limited to: a pre-loaded spring action, a hydraulic action due to fluid pressure, or a mechanical linkage with the barrel end that causes the locking bar or bars to be engaged with the locking slot or barrel end flange or like recess or structure upon which a locking bar may gain purchase to resist upward motion of the mobile component.

In other embodiments, the valve mechanism may consist of motion of at least one locking bar between a position where the port is unobstructed to fluid flow, and a position where the port is closed to fluid flow. In yet other embodiments, there may be multiple locking bars that upon retracting to a retracted position close the port to fluid flow and upon extension to a locked position open or come apart in a manner that opens the port. The release mechanism may be any structure arranged on or incorporated into the barrel assembly for pushing at least one locking bar from its respective locked position back into its retracted position.

In other embodiments, the mobile component may have or incorporate a locking bar interlock mechanism whereby retracting one locking bar retracts all the locking bars together. There are numerous mechanisms for doing this such as but not limited to a gear set or a rotational linkage where all locking bars connect or are pulled inward by a rotatable concentric ring. The function of such an interlock mechanism may be configured to extending all locking bars with the extension of any one locking bar. The locking bars may be independently or collectively spring biased for extension, so that they will extend if brought into alignment with a locking slot in the wall of the barrel, which means any recess or structural anomaly in the wall surface that will accommodate extension of a locking bar in such a way as to restrict or inhibit further longitudinal motion of the mobile component . . . .

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A safety syringe comprising:
   a barrel; a plunger; and a mobile component;
   the barrel having a proximal end and a distal end, the distal end configured with a mobile component stop and a needle opening;
   the plunger being configured with a plunger stopper slidingly and sealingly engaged within the barrel, and a plunger handle extended from the proximal end of the barrel by which the plunger stopper may be moved longitudinally within the barrel;
   the mobile component being slidingly and sealingly engaged within the barrel and configured with a port connecting an inboard face facing the plunger stopper with an outboard face facing the distal end of the barrel, the outboard face being configured to accept attachment of a needle whereby an axial bore through the needle is in communication with the port;
   the mobile component and the barrel being cooperatively configured with a lock and release mechanism whereby the mobile component is lockable in a fixed position at the distal end of and within the barrel, the port having a valve mechanism operable to open and close the port to fluid flow;
   the lock and release mechanism being configured with at least one locking bar extendable radially outward by operation of the plunger for engagement with the barrel for locking the mobile component in place; and
   the valve mechanism comprising motion of the at least one locking bar between a position where the port is unobstructed and a position where the port is closed.

2. The syringe of claim 1, wherein the locking bar is retractable inward by operation of an externally accessible release mechanism on the barrel for releasing.

3. The syringe of claim 1, the at least one locking bar comprising a plurality of locking bars that upon retracting to a retracted position close the port, and upon extension to a locked position open the port.

4. The syringe of claim 3, the release mechanism comprising a structure arranged for pushing at least one locking bar from its respective locked position to its retracted position.

5. The syringe of claim 4, wherein retracting one locking bar includes retracting all locking bars.

6. The syringe of claim 5, wherein extending one locking bar includes extending all locking bars.

7. The syringe of claim 1, said lock and release mechanism comprising at least one locking slot in the wall of said barrel at its distal end for the engagement with the barrel of the at least one locking bar.

8. The syringe of claim 7, said locking bar being spring loaded for extension whereby radial alignment of said locking bar with said locking slot permits the locking bar to extend, thereby locking said mobile component in place within said barrel.

9. The syringe of claim 7, said locking bar being spring loaded for extension whereby radial alignment of said locking bar with said locking slot permits the locking bar to extend, thereby locking said mobile component in place within said barrel and opening said port for fluid flow.

10. The syringe of claim 1 wherein said needle is attached to the mobile component.

11. The syringe of claim 10, the barrel being at least as long as the plunger stopper and mobile component with the needle attached.

12. The syringe of claim 1, said lock and release mechanism and said valve mechanism being cooperatively linked such that opening of the port to fluid flow occurs with locking of the mobile component in the fixed position and closing of the port to fluid flow occurs with release of the mobile component for longitudinal motion.

13. A safety syringe comprising:
    a barrel; a plunger; and a mobile component;
    the barrel having a proximal end and a distal end, the distal end being configured with a mobile component stop and a needle opening;
    the plunger being configured with a plunger stopper slidingly and sealingly engaged within the barrel and a plunger handle extended from the proximal end of the barrel by which the plunger stopper may be moved longitudinally within the barrel;
    the mobile component being slidingly and sealingly engaged within the barrel and configured with a port connecting an inboard face facing the plunger stopper with an outboard face facing the distal end of the barrel, the outboard face being configured to accept attachment of a needle whereby an axial bore through the needle is in communication with the port;

the mobile component and the barrel being cooperatively configured with a lock and release mechanism whereby the mobile component is lockable in a fixed position at the distal end of and within the barrel and is releasable thereafter for longitudinal motion within the barrel, the port having a valve mechanism operable to open and close the port to fluid flow; and the lock and release mechanism being configured with at least one locking bar and a spring configured for extending the locking bar radially outward for engagement with locking slots in the barrel for locking the mobile component in place when the locking bar is radially aligned therewith, and the barrel being configured with an externally accessible release mechanism on the barrel for depressing the at least one locking bar inward out of its respective locking slot in the barrel, thereby releasing the mobile component for longitudinal motion.

14. The syringe of claim 13, the valve mechanism comprising motion of the at least one locking bar between a position where the port is unobstructed and a position where the port is closed, whereby the locking of the mobile component in place causes opening of the port to fluid flow and releasing the mobile component for longitudinal motion closes the port to fluid flow.

15. The syringe of claim 1, the barrel and plunger cooperatively configured with a plunger lock by which the plunger may be restrained from longitudinal motion relative to the barrel.

16. A safety syringe comprising:

a barrel; a plunger; a mobile component; and a needle;

the barrel having a proximal end and a distal end, the distal end configured with a mobile component stop and a needle opening;

the plunger configured with a plunger stopper slidingly and sealingly engaged within the barrel and a plunger handle extended from the proximal end of the barrel by which the plunger stopper may be moved longitudinally within the barrel;

the mobile component being slidingly and sealingly engaged within the barrel and configured with a port connecting an inboard face facing the plunger stopper with an outboard face facing the distal end of the barrel, the needle being attached to the outboard face whereby an axial bore through the needle is in communication with the port;

the mobile component and the barrel cooperatively configured with a lock and release mechanism whereby the mobile component is lockable in a fixed position at the distal end of and within the barrel and is releasable thereafter for longitudinal motion within the barrel, the port having a valve mechanism operable to open and close the port to fluid flow;

the lock and release mechanism and the valve mechanism being cooperatively linked such that opening of the port to fluid flow occurs with locking of the mobile component in the fixed position and closing of the port to fluid flow occurs with release of the mobile component for longitudinal motion.

17. The syringe of claim 16, the lock and release mechanism comprising the mobile component being configured with at least one locking bar and a spring configured for extending the locking bar radially outward for engagement with locking slots in the barrel for locking the mobile component in place when the locking bar is radially aligned therewith, and the barrel being configured with an externally accessible release mechanism on the barrel for depressing the at least one locking bar inward out of its respective locking slot in the barrel, thereby releasing the mobile component for longitudinal motion.

18. The syringe of claim 16, the valve mechanism comprising motion of the at least one locking bar between a position where the port is unobstructed and a position where the port is closed, whereby the locking of the mobile component in place causes opening of the port to fluid flow and releasing the mobile component for longitudinal motion closes the port to fluid flow.

19. The syringe of claim 16, the barrel being at least as long as the plunger stopper and mobile component with the needle attached.

* * * * *